United States Patent
Hsu et al.

(10) Patent No.: US 10,357,401 B2
(45) Date of Patent: Jul. 23, 2019

(54) ELASTIC TENSION CHANGING HEADBAND

(71) Applicant: Disney Enterprises, Inc., Burbank, CA (US)

(72) Inventors: Jonathan R. Hsu, Pomona, CA (US); Philippe Putzeys, Los Angeles, CA (US)

(73) Assignee: Disney Enterprises, Inc., Burbank, CA (US)

( * ) Notice: Subject to any disclaimer, the term of this patent is extended or adjusted under 35 U.S.C. 154(b) by 314 days.

(21) Appl. No.: 15/282,983

(22) Filed: Sep. 30, 2016

(65) Prior Publication Data
US 2018/0095497 A1 Apr. 5, 2018

(51) Int. Cl.
| | |
|---|---|
| *A42B 1/22* | (2006.01) |
| *A43C 11/00* | (2006.01) |
| *A44B 1/04* | (2006.01) |
| *A44B 11/25* | (2006.01) |
| *A61F 9/06* | (2006.01) |
| *A42B 3/08* | (2006.01) |
| *A41D 13/11* | (2006.01) |
| *A42B 3/14* | (2006.01) |
| *G02B 27/01* | (2006.01) |

(52) U.S. Cl.
CPC .............. *A61F 9/06* (2013.01); *A42B 3/085* (2013.01); *A41D 13/1161* (2013.01); *A42B 3/145* (2013.01); *G02B 2027/0178* (2013.01)

(58) Field of Classification Search
CPC .... A41D 13/1161; A41D 20/00; A42B 3/145; A42B 1/22; A42B 3/14; A42B 3/085; A42B 3/324; A42B 3/142; Y10T 24/2187

USPC ........................... 2/417, 418, 421, 183, 195.4
See application file for complete search history.

(56) References Cited

U.S. PATENT DOCUMENTS

| | | | | |
|---|---|---|---|---|
| 2,205,742 A | * | 6/1940 | Bowers ................. | A42B 3/145 2/418 |
| 2,437,748 A | * | 3/1948 | Malcom ................. | A42B 3/145 2/183 |
| 5,357,654 A | * | 10/1994 | Hsing-Chi ............. | A42B 3/145 2/418 |
| 5,845,341 A | * | 12/1998 | Barthold ................. | A42B 3/04 2/424 |
| 6,314,588 B1 | * | 11/2001 | Fang ....................... | A42B 3/145 2/183 |

(Continued)

*Primary Examiner* — Jameson D Collier
(74) *Attorney, Agent, or Firm* — Patterson + Sheridan, LLP

(57) ABSTRACT

Embodiments provide a retention apparatus for a head-mounted device and a head-mounted apparatus including the retention apparatus and the head-mounted device. The retention apparatus includes left and right band portions arranged on respective sides of a user's head, which connect to the head-mounted device at one end, and include opposing free ends that are arrangeable toward a back side of the wearer's head. The retention apparatus includes left and right elastic straps and an adjustment mechanism. The adjustment mechanism is arrangeable at the back of the user's head and includes arms the telescope into and out of the adjustment mechanism. The elastic straps are attached to the left and right band portions at first ends and to respective arms of the adjustment mechanism at second ends. Adjustably moving the arms of the adjustment mechanism stretches or relaxes the elastic straps, adjusting tension of the retention apparatus.

20 Claims, 8 Drawing Sheets

(56) References Cited

U.S. PATENT DOCUMENTS

| | | | | |
|---|---|---|---|---|
| 7,707,695 B2* | 5/2010 | Dubois | ............... | A42B 3/145 |
| | | | | 2/418 |
| 8,032,993 B2* | 10/2011 | Musal | ................. | A42B 3/145 |
| | | | | 2/418 |
| 8,161,576 B2* | 4/2012 | Lemke | ................... | A61F 9/06 |
| | | | | 2/417 |
| 9,161,588 B2* | 10/2015 | Chen | ................... | A42B 3/145 |
| 2008/0295229 A1* | 12/2008 | Fang | ................... | A42B 3/145 |
| | | | | 2/418 |
| 2015/0074876 A1* | 3/2015 | Chiang | ............... | A42B 3/145 |
| | | | | 2/418 |
| 2017/0055623 A1* | 3/2017 | Pritz | ................... | A42B 3/145 |
| 2017/0245577 A1* | 8/2017 | Zhang | ................ | A42B 3/085 |

* cited by examiner

ELASTIC TENSION CHANGING HEADBAND

BACKGROUND

Virtual/augmented/mixed reality headsets typically include a housing, electronics, and display arranged in front of a user's eyes to display a computer-generated environment to the user. In many instances, the computer-generated environment is interactive, meaning that a view presented to the user changes as the user moves his head to look up, look down, look right, or look left, for example. Additionally, motion tracking (e.g., through exterior sensors and/or built in attitude sensors) can track translation of the user's head, such as the user raising his head (e.g., standing up), lowering his head (e.g., sitting down or squatting), or translating his head (e.g., walking). Many virtual reality applications take advantage of such head tracking to enable the user to control aspects of the application. However, such head movements create loads on the virtual reality headset.

To prevent the virtual reality headset from slipping or otherwise moving relative to the user's head as the user moves his head to interact with the computer generated environment, the virtual reality headset is sometimes secured to the user's head with semi-rigid, resilient band portions (e.g., plastic bands) that bend but do not appreciably stretch. For example, a virtual reality headset may have a first band portion extending from a left side of the virtual reality headset and a second band portion extending from a right side of the virtual reality headset. The first and second band portions extend around on opposite sides of the user's head such that the first and second bands overlap at the rear of the user's head. The first band portion, second band portion, and virtual reality headset form a complete perimeter around a portion of the user's head. The amount of overlap is typically adjustable by an adjustment mechanism. By adjusting the amount of overlap between the first band portion and the second band portion, the perimeter formed by the first band portion, second band portion, and virtual reality headset can be increased or decreased in length, thereby loosening or tightening, respectively, the band portions about the user's head.

Such stiff, resilient band portions can be uncomfortable for a user to wear for a long period of time. For example, as discussed above, the user may adjust the overlap between the first and second band portions to properly fit on the user's head. However, the user may make facial movements while wearing the virtual reality headset that change the geometry of the user's head. For example, the user may talk, raise his eyebrows, yawn, or cough, any of which may momentarily change the size of the user's head. During such momentary changes, the first and second band portions may be uncomfortably tight about the user's head or may become loose such that the virtual reality headset slips or moves relative to the user's head.

SUMMARY

Embodiments provide a retention apparatus for supporting a head-mounted device. The retention apparatus comprises a left band portion configured for arrangement along a left side of a wearer's head. The left band portion comprises a resilient material. The left band portion includes a first device end configured for attachment to a head-mounted device and a first free end portion configured for arrangement toward a back side of the wearer's head. The retention apparatus also comprises a right band portion configured for arrangement along a right side of the wearer's head. The right band portion comprises the resilient material. The left band portion includes a second device end configured for attachment to a head-mounted device and a second free end portion configured for arrangement toward a back side of the wearer's head. The retention apparatus also comprises an adjustment mechanism configured for arrangement at the back of the wearer's head. The adjustment mechanism includes an adjustment housing, a first arm, and a second arm, and wherein the first arm and second arm are selectively adjustable into and out of the adjustment housing in a telescoping manner. The retention apparatus also comprises a left elastic strap that includes a first end and an opposing second end. The first end is connected to the left band portion. The second end is connected to the first arm of the adjustment mechanism. The retention apparatus also comprises a right elastic strap that includes a third end and an opposing fourth end. The third end is connected to the right band portion. The fourth end is connected to the second arm of the adjustment mechanism. Selective adjustment of the first and second arms into the adjustment housing increases tension on the left and right elastic straps and thereby pulls the first and second free end portions of the respective left and right band portions toward each other. Selective adjustment of the first and second arms out of the adjustment housing decreases tension on the left and right elastic straps and thereby enable the first and second free end portions of the respective left and right band portions to move apart.

Embodiments provide a head-mounted apparatus. The head-mounted apparatus comprises a face-mounted device configured for arrangement over at least a portion of a wearer's face. The head-mounted apparatus also comprises a left band portion configured for arrangement along a left side of a wearer's head. The left band portion comprises a resilient material. The left band portion includes a first device end attached to a left side of the face-mounted device and a first free end portion, opposite the first device end, configured for arrangement toward a back side of the wearer's head. The head-mounted apparatus also comprises a right band portion configured for arrangement along a right side of the wearer's head. The right band portion comprises the resilient material. The left band portion includes a second device end attached to a right side of the face-mounted device and a second free end portion, opposite the second device end, configured for arrangement toward a back side of the wearer's head. The head-mounted apparatus also comprises an adjustment mechanism configured for arrangement at the back of the wearer's head. The adjustment mechanism includes an adjustment housing, a first arm, and a second arm, and wherein the first arm and second arm are selectively adjustable into and out of the adjustment housing in a telescoping manner. The head-mounted apparatus also comprises a left elastic strap that includes a first end and an opposing second end. The first end is connected to the left band portion. The second end is connected to the first arm of the adjustment mechanism. The head-mounted apparatus also comprises a right elastic strap that includes a third end and an opposing fourth end. The third end is connected to the right band portion. The fourth end is connected to the second arm of the adjustment mechanism. Selective adjustment of the first and second arms into the adjustment housing increases tension on the left and right elastic straps and thereby pulls the first and second free end portions of the respective left and right band portions toward each other. Selective adjustment of the first and second arms out of the adjustment housing decreases tension on the left and right elastic straps and thereby enable the first and second free end portions of the respective left and right band portions to move apart.

Embodiments provide a head-mounted apparatus. The head-mounted apparatus comprises a head band that includes a left band portion configured for arrangement along a left side of a wearer's head, a right band portion configured for arrangement along a left side of the wearer's head, and a forehead portion configured for arrangement along the wearer's forehead. The head band comprises a resilient material. The left band portion includes a first free end portion configured for arrangement toward a back side of the wearer's head. The right band portion includes a second free end portion configured for arrangement toward a back side of the wearer's head. The head-mounted apparatus also comprises a face-mounted device connected to the forehead portion of the head band and configured for arrangement over at least a portion of a wearer's face. The head-mounted apparatus also comprises an adjustment mechanism configured for arrangement at the back of the wearer's head. The adjustment mechanism includes an adjustment housing, a first arm, and a second arm. The first arm and second arm are selectively adjustable into and out of the adjustment housing in a telescoping manner. The head-mounted apparatus also comprises a left elastic strap that includes a first end and an opposing second end. The first end is connected to the left band portion. The second end is connected to the first arm of the adjustment mechanism. The head-mounted apparatus also comprises a right elastic strap that includes a third end and an opposing fourth end. The third end is connected to the right band portion. The fourth end is connected to the second arm of the adjustment mechanism. Selective adjustment of the first and second arms into the adjustment housing increases tension on the left and right elastic straps and thereby pulls the first and second free end portions of the respective left and right band portions toward each other. Selective adjustment of the first and second arms out of the adjustment housing decreases tension on the left and right elastic straps and thereby enable the first and second free end portions of the respective left and right band portions to move apart.

BRIEF DESCRIPTION OF THE DRAWINGS

So that the manner in which the above recited aspects are attained and can be understood in detail, a more particular description of embodiments of the invention, briefly summarized above, may be had by reference to the appended drawings.

It is to be noted, however, that the appended drawings illustrate only typical embodiments of this invention and are therefore not to be considered limiting of its scope, for the invention may admit to other equally effective embodiments.

DETAILED DESCRIPTION

In embodiments described herein, free ends of a semi-rigid headband for a virtual reality headset or other head-mounted device are not coupled to one another via an adjustment mechanism. Rather, an adjustment mechanism positioned at the rear of the user's head is connected to a left band portion and a right band portion of the semi-rigid headband via elastic straps. When the virtual reality headset or other head-mounted device is worn by a user, arms of the adjustment mechanism telescopically lengthen or reduce a distance spanned by the elastic material between attachment points on the left and right band portions and the adjustment mechanism. Such stretching or relaxing of the elastic material increases or decreases tension, respectively, to the left and right band portions, which is transmitted to the user's head. As a result, the headband may be tightened or loosened about the user's head. Furthermore, in the event the user performs an action that momentarily changes the geometry of his head (e.g., talking, laughing, yawning, or coughing), the elastic material can stretch or shrink such that the headband comfortably conforms to the momentarily changed geometry of the user's head.

Figure 1:
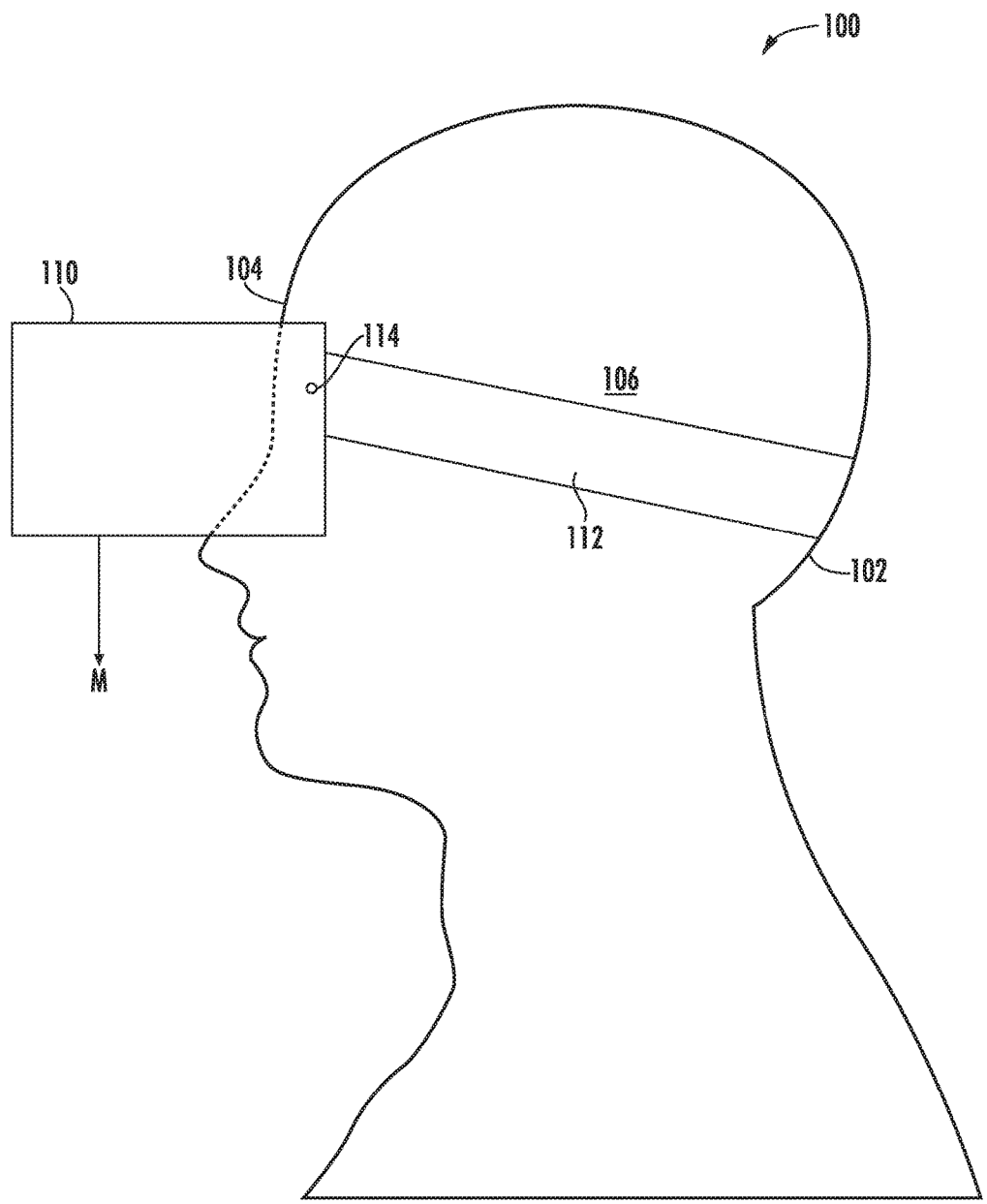
FIG. 1 is a side view of a human head with virtual reality goggles arranged in front of the eyes of the head and a band wrapped around the head, supporting the goggles.
Figure 2A:
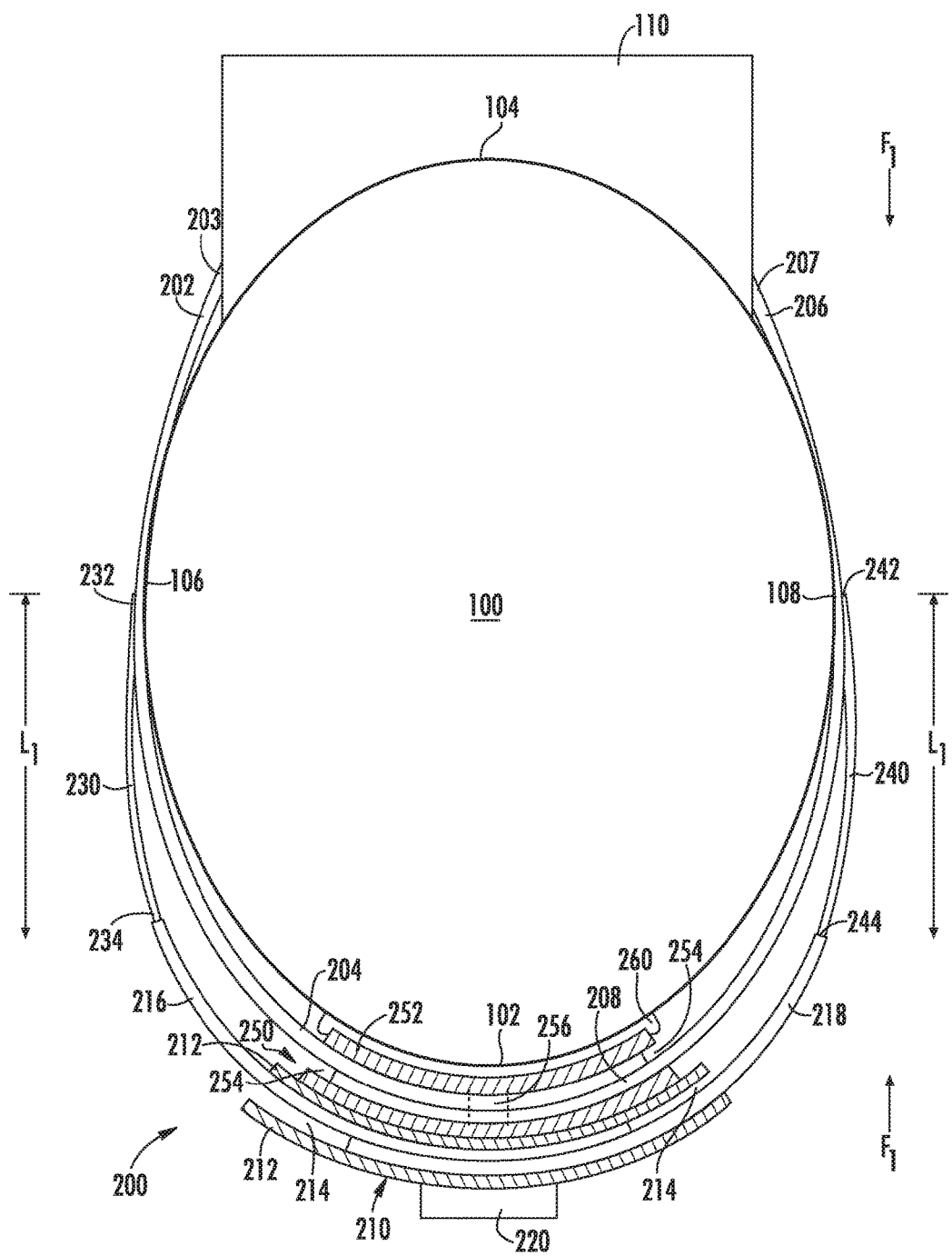
FIG. 2A is a top, partial cross-sectional view of the head of FIG. 1 with the virtual reality goggles arranged in front of the eyes of the head, and a band according to one embodiment wrapped around the user's head, wherein the band is illustrated in a first adjustment position.

FIG. 1 is a side view of a head 100 of a user wearing a head-mounted device 110 (e.g., a virtual reality headset). The head-mounted device 110 includes a mass M (a gravitational force on which is indicated by arrow M) arranged in front of the forehead 104 of the user. The head-mounted device 110 is secured to the user's head 100 by a band 112 that wraps around sides of the user's head (the left side 106 of the head 100 is visible in FIG. 1) to the back 102 of the user's head 100. The band 112 may be fixedly attached to the head-mounted device 110 or, as shown in FIG. 1, may be attached to the head-mounted device 110 by a pivot 114 (e.g., a hinge). The pivot 114 enables rotation of the head-mounted device 110 relative to the band 112 about a central axis that is normal to the plane of FIG. 1, FIG. 2A is a top view of the user's head 100 wherein the head-mounted device 110 is secured to the user's head 100 via a retention apparatus 200, according to one embodiment. The retention apparatus 200 replaces the band 112, shown in FIG. 1. The retention apparatus 200 includes a left band portion 202 arranged along the left side 106 of the user's head 100 and a right band portion 206 arranged along the right side 108 of the user's head 100. The left band portion 202 and the right band portion 206 are made of a semi-rigid, resilient material, such as a plastic or polymer material (e.g., nylon, poly-vinyl chloride, or a carbon fiber reinforced plastic). The semi-rigid, resilient material may flex, but does not appreciably stretch (i.e., yield) when exposed to forces that may be safely experienced while on the user's head 100. The left band portion 202 and the right band portion 206 may include at least a certain amount of curvature to match the curvature of a user's head 100. In at least one embodiment, the curvature can be matched to a specific user's head. In at least one other embodiment, the curvature can be matched to a "generalized" or "average" head. The resilient nature of the left hand portion 202 and the right band portion 206 allows for flexing of the left band portion 202 in the right band portion 206 for conformance to a particular user's head.

The left band portion 202 includes a first device end 203 that is attached to a left side of the head-mounted device 110 and the right band portion 206 includes a second device end 207 that is attached to a right side of the head-mounted device 110. The left band portion 202 includes a first free end portion 204 arranged toward the back 102 of the user's head 100 and the right band portion 206 includes a second free end portion 208 arranged toward the back 102 of the user's head 100. As shown in FIG. 2A, the first free end portion 204 and the second free end portion 208 overlap at the back 102 of the user's head 100. In other embodiments, the first free end portion 204 and the second free end portion 208 may not overlap. For example, the first free end portion 204 may terminate before reaching the back 102 of the user's head 100 and the second free end portion 208 may terminate before reaching the back 102 of the user's head 100 such that the free end portions 204 and 208 do not overlap.

Figure 3:
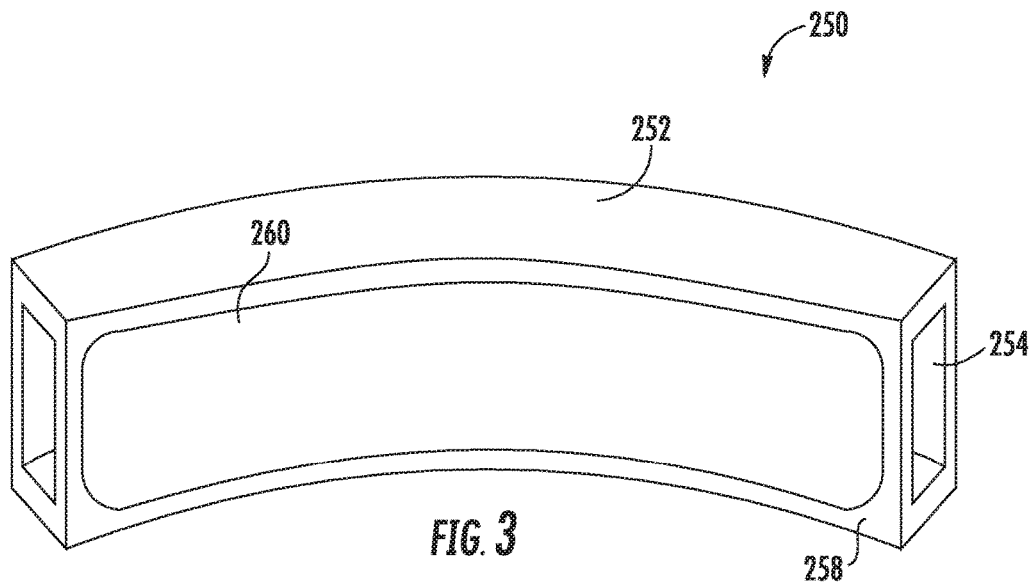
FIG. 3 is a perspective view of a band housing of the band illustrated in FIG. 2A.

The first free end portion 204 and the second free end portion 208 are arranged in a band housing 250, which is best illustrated with simultaneous reference to FIG. 2A and FIG. 3. The band housing 250 includes a housing 252 with a channel 254 therethrough. The band housing 250 has a curved shape to match a contour of the back 102 of the user's head 100. The channel 254 includes a curved path that generally follows the curved shape of the band housing 250. The curved shape of the band housing 250 may be matched to a particular user's head or may be based on a "generalized" or "average" head. The first free end portion 204 and the second free end portion 208 are loosely fit through the channel 254 in the housing 252 such that the first free end portion 204 and the second free end portion 208 can slide into and out of the channel 254 relative to each other to increase or decrease a total length of a perimeter formed by the left band portion 202, the right band portion 206, and the head-mounted device 110 about the user's head 100. The band housing 250 can optionally include a pin 256 arranged transversely with respect to the channel 254 such that the pin 256 engages slots in the first free end portion 204 and the second free end portion 208. The pin 256 can limit a range of motion of the first free end portion 204 and the second free end portion 208 relative to the band housing 250. The pin 256 and the slots in the first free end portion 204 and the second free end portion 208 are discussed in greater detail with reference to FIGS. 4A-4C.

The band housing 250 may optionally include padding material 260 covering at least a portion of the housing 252. In one embodiment, at least a portion of a surface of the housing 252 facing the back 102 of the user's head 100 are covered in the padding material 262 provide comfort and surface conformance with the back 102 of the user's head 100.

An adjustment mechanism 210 is attached to the band housing 250. In the embodiment shown in FIG. 2A, the adjustment mechanism 210 is attached to the band housing 250 such that the band housing 250 is between the adjustment mechanism 210 and the user's head 100. The adjustment mechanism 210 may include a curved shape that matches the curved shape of the band housing 250. The adjustment mechanism 210 includes an adjustment housing 212 with a channel 214 arranged there through. A first arm 216 and a second arm 218 are arranged partially within the channel 214 in the adjustment housing 212. The first arm 216, the second arm 218, and the channel 214 include curved profiles that generally match the curved shape of the adjustment mechanism 210. The first arm 216 and the second arm 218 are adjustably slidable into and out of the channel 214 in the adjustment housing 212 in a telescoping manner. The adjustment mechanism 210 includes an adjustment knob 220 arranged on the adjustment housing 212. As discussed in greater detail below with reference to FIGS. 5A-5B, rotation of the adjustment knob 220 in a first direction causes the first arm 216 and the second arm 218 to move out of the housing in a telescoping manner, and rotation of the adjustment knob 220 and a second direction causes the first arm 216 and the second arm 218 to move into the housing in a telescoping manner. The first and second arms are semi-rigid, resilient material, such as a plastic or polymer material (e.g., nylon or a carbon fiber reinforced plastic).

The first arm 216 of the adjustment mechanism 210 is attached to the left band portion 202 by a left elastic strap 230. A first end 232 of the left elastic strap 230 is connected to the left band portion 202 and an opposing second end 234 of the left elastic strap 230 is connected to the first arm 216 of the adjustment mechanism 210. The second arm 218 of the adjustment mechanism 210 is attached to the right band portion 206 by a right elastic strap 240. A third end 242 of the right elastic strap 240 is connected to the right band portion 206 and an opposing fourth end 244 of the right elastic strap 240 is connected to the second arm 218 of the adjustment mechanism 210. In one embodiment, the first end 232 of the left elastic strap 230 is connected to the left band portion 202 at a position along the left band portion 202 between the first device end 203 and a location over the left ear of the user's head 100. Similarly, the third end 242 of the right elastic strap 240 is connected to the right band portion 206 at a position along the right band portion 206 between the second device and 207 and a location over the right ear of the user's head 110. In another embodiment, the first end 232 of the left elastic strap 230 is connected to the left band portion 202 at a location along the left band portion 202 over the left temple of the user's head 100. Similarly, the third end 242 of the right elastic strap 240 is connected to the right band portion 206 at a location along the right band portion 206 over the right temple of the user's head 100.

The left elastic strap 230 and the right elastic strap 240 are typically made of an elastic fabric material. For example, the left elastic strap 230 and the right elastic strap 240 may be made of a fiber that includes a rubber or spandex core wrapped in polyester, nylon, or cotton, which is then woven, knitted, or braided to create elastic fabric. In various other embodiments, the left elastic strap 230 and the right elastic strap 240 may be made of other elastic materials, such as rubber straps, bungee cords, or metallic springs.

Figure 2B:
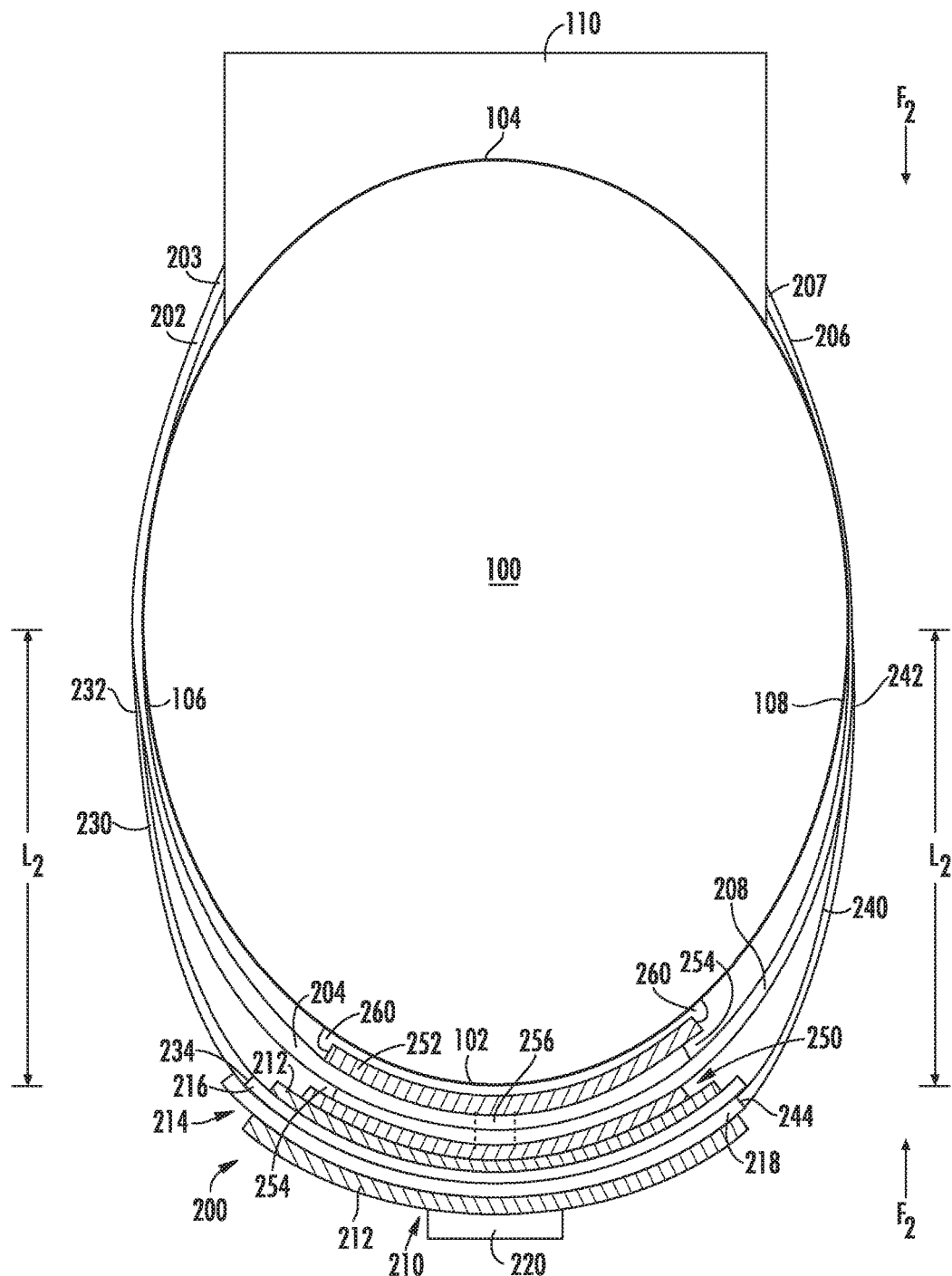
FIG. 2B is a top, partial cross-sectional view of the head of FIG. 1 with the virtual reality goggles arranged in front of the eyes of the head, and the band of FIG. 2A wrapped around the user's head, wherein the band is illustrated in a second adjustment position.

When the first arm 216 and the second arm 218 of the adjustment mechanism 210 move telescopically into or out of the adjustment housing 212, a length of the left elastic strap 230 and the right elastic strap 240 changes. For example, FIG. 2A illustrates the adjustment mechanism 210 with the first arm 216 and the second arm 218 telescoped out of the adjustment housing 212 and FIG. 2B illustrates the adjustment mechanism 210 with the first arm 216 and the second arm 218 telescoped in to the adjustment housing 212 (relative to the position of the first arm 216 and the second arm 218 illustrated in FIG. 2A). As a result, the left elastic strap 230 and the right elastic strap 240 are stretched to a length of $L_1$ in FIG. 2A and are stretched to a length $L_2$ in FIG. 2B, wherein the length $L_2$ is greater than the length of $L_1$. The elastic straps 230 and 240 resist stretching with a restoring force that is proportional to the degree with which elastic straps 230 and 240 are stretched. Stated differently, when ends of the elastic straps 230 and 240 are stretched apart from a resting, unstretched state, the elastic straps 230 and 240 exert a restoring force to return to the resting, unstretched state once the stretching force is terminated. The restoring force increases as the ends of the elastic straps 230 and 240 are stretched further apart. The restoring force of the left elastic strap 230 and the right elastic strap 240 is transmitted to the adjustment mechanism 210 and the band housing 250 via the first arm 216 and the second arm 218, and is transmitted to the head-mounted device 110 via the left band portion 202 and the right band portion 206. In FIG. 2A, wherein the left elastic strap 230 and the right elastic strap 240 are stretched to the length $L_1$, the restoring forces of the left elastic strap 230 and the right elastic strap 240 result in a force $F_1$ being applied to the user's head 100 by the head-mounted device 110 and the band housing 250. In FIG. 2B, where the left elastic strap 230 and the right elastic strap 240 are stretched to the length $L_2$ (greater than the length $L_1$), the restoring forces of the left elastic strap 230 and the right elastic strap 240 result in a force $F_2$ (greater than the force $F_1$) being applied to the user's head 100 by the head-mounted device 110 and the band housing 250.

The user can adjust the above-described tension applied by the retention apparatus 200 and the head-mounted device 110 by using the adjustment knob 220 to telescopically move the first arm 216 and the second arm 218 into or out of the adjustment housing 212 of the adjustment mechanism 210. Such tension adjustment allows the user to set the tension to a level that provides an adequate degree of retention of the head-mounted device 110 on the user's head 100 while still being comfortable. Additionally, if the user performs a movement that temporarily changes the geometry of the head 110 (e.g., yawning, coughing, or talking), the stretched length of the left elastic strap 230 and the right elastic strap 240 can also temporarily change to accommodate the changed geometry. As a result, the head-mounted device 110 remains secure during such temporary changes to the geometry of the head 110 and the retention apparatus 200 remains comfortable during such temporary changes to the geometry of the head 110.

FIG. 3 is a detail, perspective front view of the band housing 250 of the retention apparatus 200. The band housing 250 includes a housing 252 with the channel 254 therethrough. The cushion material 260 is arranged on at least a portion of a surface 258 that faces the back 102 of the user's head 100. As discussed above, the housing 252 and the channel 254 therethrough curve to match a profile of the user's head 100. The first free end 204 of the left band portion 202 and the second free end 208 of the right band portion 206 that are inserted into the channel 254 have a curved profile similar to or the same as the curvature through the channel 254.

Figure 4A:
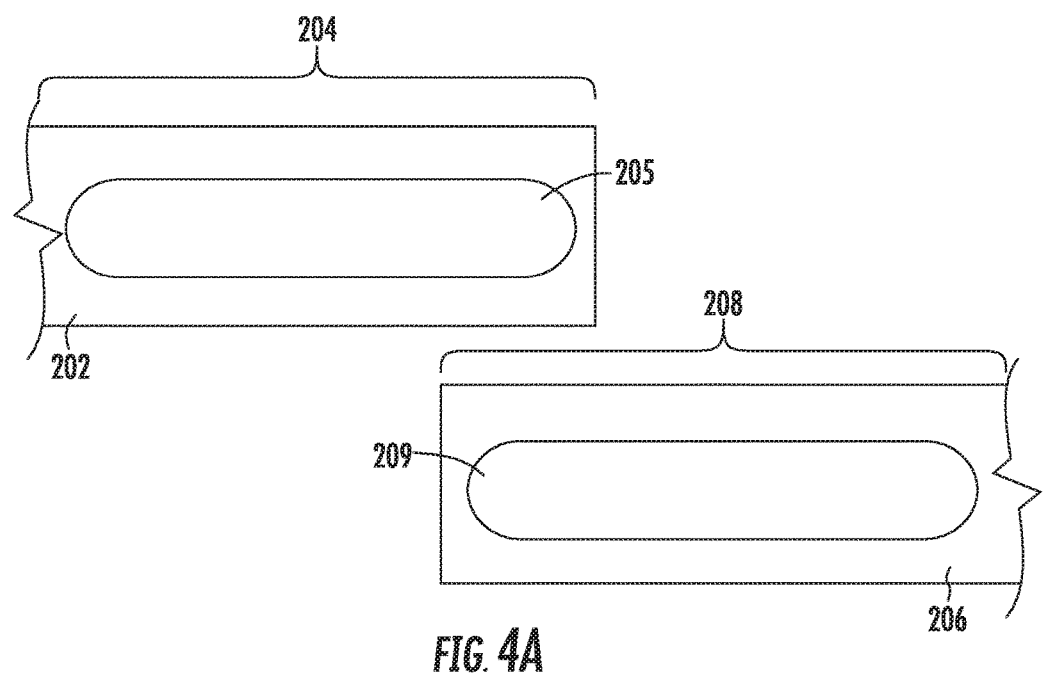
FIG. 4A is a plan view of free ends of a first band portion and a second band portion of the band illustrated in FIG. 2A, wherein the free ends of the first and second band portions include slots.

FIG. 4A is a front view of the first free end 204 of the left band portion 202 and the second free end 208 of the right band portion 206 shown spaced apart for clarity. The first free end 204 of the left band portion 202 includes a first slot 205 arranged therethrough and the second free end 208 of the right band portion 206 includes a second slot 209 arranged therethrough. As illustrated in FIG. 4A, in at least one embodiment, the first slot 205 and the second slot 209 have oval shapes. In other embodiments, the first slot 205 and the second slot 209 have different shapes.

Figure 4B:
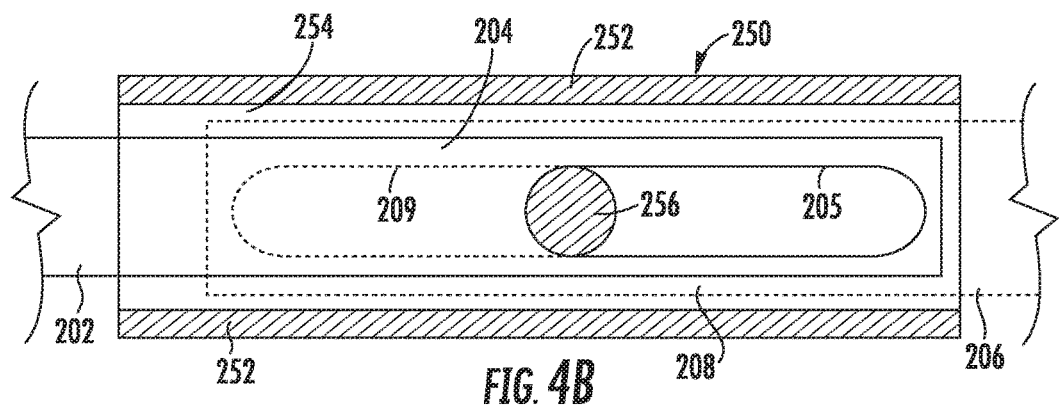
FIG. 4B is a plan view of the free ends of FIG. 4A illustrated in an overlapping manner with a pin of the band housing extending through the slots, wherein the first and second band portions are shown at a first overlap limit.
Figure 4C:
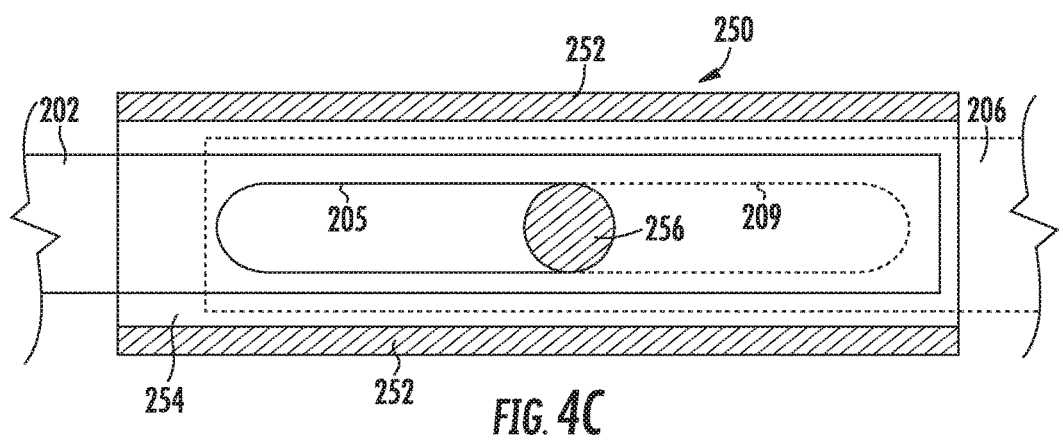
FIG. 4C is a plan view of the free ends of FIG. 4A in an overlapping manner with the pin of the band housing extending through the slots, wherein the first and second band portions are shown at a second overlap limit that is opposite the first overlap limit.

FIGS. 4B and 4C illustrate a front cross-sectional view of the band housing 250 with the first free end 204 of the left band portion 202 and the second free end 208 of the right band portion 206 overlapping in the channel 254. For clarity, the second free end 208 of the right band portion 206 is illustrated in broken line and with slightly larger dimensions to be visually distinguishable from the first free end 204 of the left band portion 202. The first slot 205 and the second slot 209 overlap in the channel 254, and the pin 256 of the band housing 250 passes through the overlapped slots 205 and 209. The pin 256 retains the first free end 204 of the left band portion 202 and the second free end 208 of the right band portion 206 within band housing 250 and also limits movement of the left band portion 202 and the right band portion 206 relative to the band housing 250. FIG. 4B illustrates the first free end 204 of the left band portion 202 and the second free end 208 of the right band portion 206 fully inserted into the band housing 250. The pin 256, engaging the first slot 205 and the second slot 209, limits further motion of the left band portion 202 and the right band portion 206. FIG. 4C illustrates the first free end 204 of the left band portion 202 and the second free end 208 of the right band portion 206 fully extended from the band housing 250. Again, the pin 256, engaging the first slot 205 in the second slot 209, limits further motion of the left band portion 202 and the right band portion 206 out of the band housing 250.

Figure 5A:
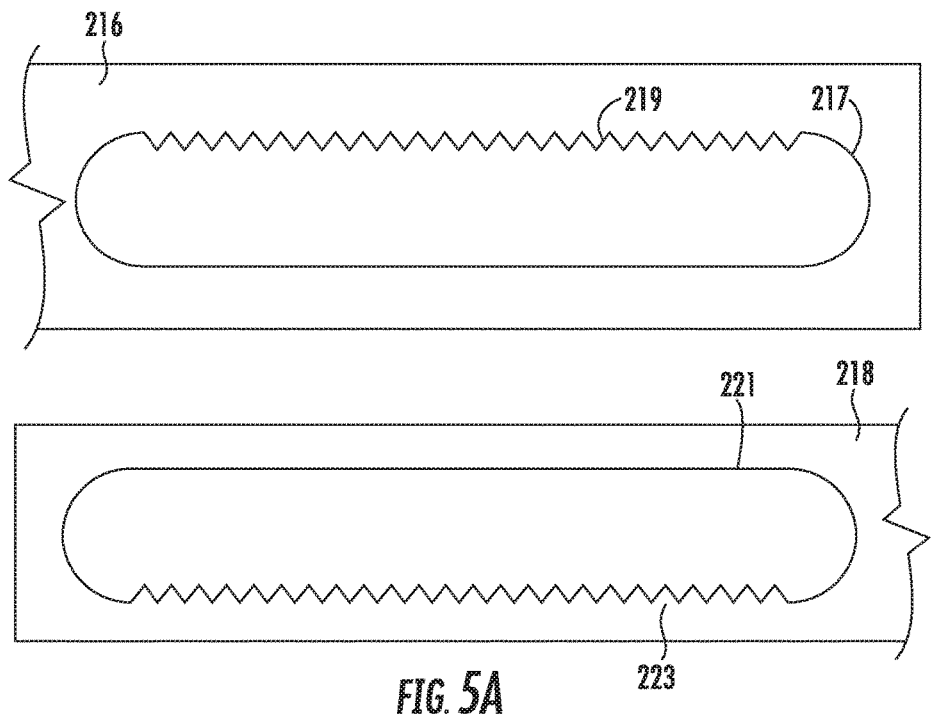
FIG. 5A is a plan view of portions of the first and second arms of an adjustment mechanism, wherein the first and second arms include slots therein, wherein the slot of the first arm includes a rack along a first edge of the slot, and wherein the slot of the second arm includes a rack along a second edge opposite the first edge.
Figure 5B:
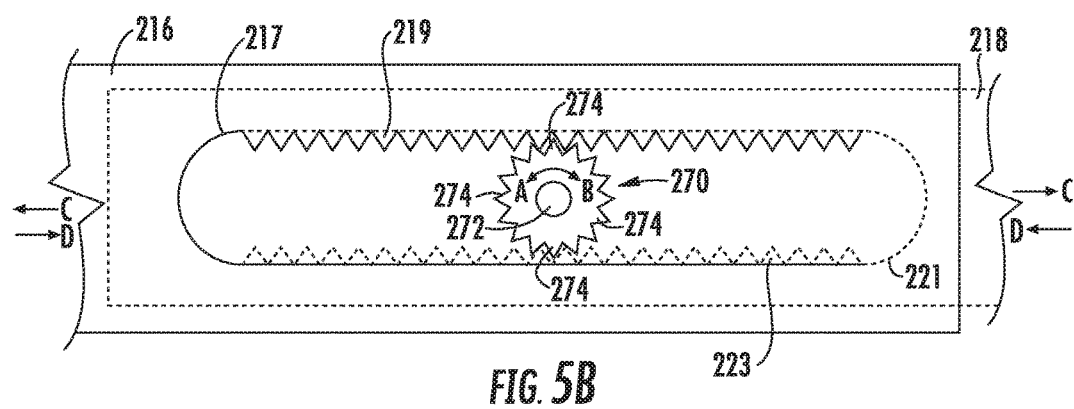
FIG. 5B is a plan view of the first and second arms of FIG. 5A arranged in an overlapping manner, wherein teeth of a gear engages the first rack and second rack.

FIGS. 5A and 5B illustrate an exemplary assembly for selective adjustment of the first arm 216 and the second arm 218 of the adjustment mechanism 210 shown in a spaced apart manner for clarity. FIG. 5A shows a portion of the first arm 216 and a portion of the second arm 218 that are arranged within the channel 214 of the adjustment housing 212 of the adjustment mechanism 210. The first arm 216 includes a slot 217 there through with a rack 219 arranged along a first edge of the slot 217. The second arm 218 includes a slot 221 there through with a rack 223 arranged along a second edge of the slot 221.

FIG. 5B illustrates the first arm 216 and the second arm 218 overlapping, as they would overlap in the channel 214 of the adjustment mechanism 210. For clarity, the components of the second arm 218 are illustrated in broken line and with slightly different dimensions to be visually distinguishable from the components of the first arm 216. Referring to FIG. 5B, when the first arm 216 and the second arm 218 overlap in the channel 214 of the adjustment housing 212, the slots 217 and 221 overlap such that the rack 219 of the first arm 216 is exposed along the first edge of the overlapping slots 217 and 221 and the rack 223 of the second arm 218 is exposed along the second edge of the overlapping slots 217 and 221. A pinion gear 270 is arranged in the slots 217 and 221 and is connected to the adjustment knob 220 via a shaft 272 such that rotation of the adjustment knob 220 results in corresponding rotation of the pinion gear 270. The pinion gear 270 includes a plurality of teeth 274 arranged there around. The teeth 274 have a size and pitch the same as or similar to a size and pitch of teeth of the racks 219 and 223. Rotation of the pinion gear 270 causes the first arm 216 and the second arm 218 to move into or out of the housing 212 of the adjustment mechanism 210. For example, if the pinion gear 270 is rotated in the direction of arrow A about the shaft 272, then the first arm 216 and the second arm 218 will move telescopically outward in the direction of arrows C. As another example, if the pinion gear 270 is rotated in the direction of arrow B about the shaft 272, then the first arm 260 and the second arm 218 will move telescopically inward in the direction of arrows D. The adjustment knob 220, the shaft 274, and/or the pinion gear 270 could include a clutch, ratchet mechanism, or other friction device that discourages motion of the first arm 216, the second arm 218, and the pinion gear 270 absent rotation of the adjustment knob 220.

Figure 6:
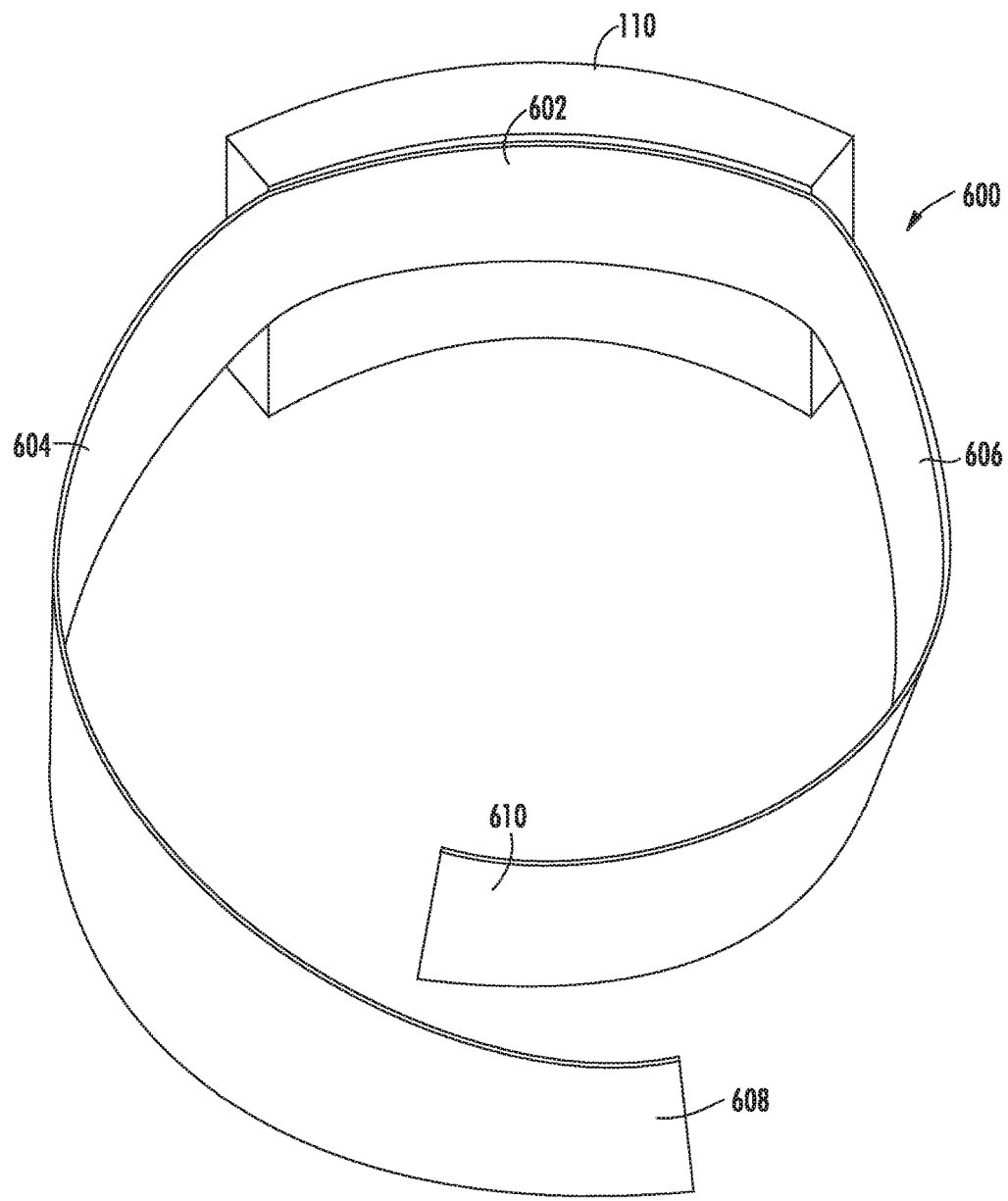
FIG. 6 is a perspective rear view of a virtual reality headset connected to a band that includes a first band portion, a second band portion and a forehead portion, wherein the first band portion, second band portion, and forehead portion are unitary.

In various embodiments, the semi-rigid, resilient band is a continuous piece about a head of the user. FIG. 6 illustrates an exemplary band 600, according to one embodiment, for supporting a head-mounted device 110 in which the band 600 includes a left band portion 604, a right band portion 606, and a forehead portion 602. For clarity, the remaining portions of the retention apparatus 200 (e.g., the adjustment mechanism 210, the band housing 250, the left elastic strap 230, and the right elastic strap 240) have been omitted. The left band portion 604 includes a first free end 608 arrangeable toward a back side of a wearer's head and the right band portion 606 includes a second free end 610 arrangeable toward the backside of the wearer's head. In at least one embodiment, the left band portion 604, the right band portion 606, and the forehead portion 602 are unitary or monolithic. The head-mounted device 110 can be attached to the forehead portion 602 via fasteners (e.g., screws or rivets) or an adhesive (e.g., epoxy or glue). The head-mounted device 110 could be attached to the forehead portion via other mechanical means. For example, the head-mounted device 110 could include a slot or channel through which the band 600 is inserted such that the forehead portion 602 of the band 600 is aligned with the head-mounted device 110.

Figure 7:
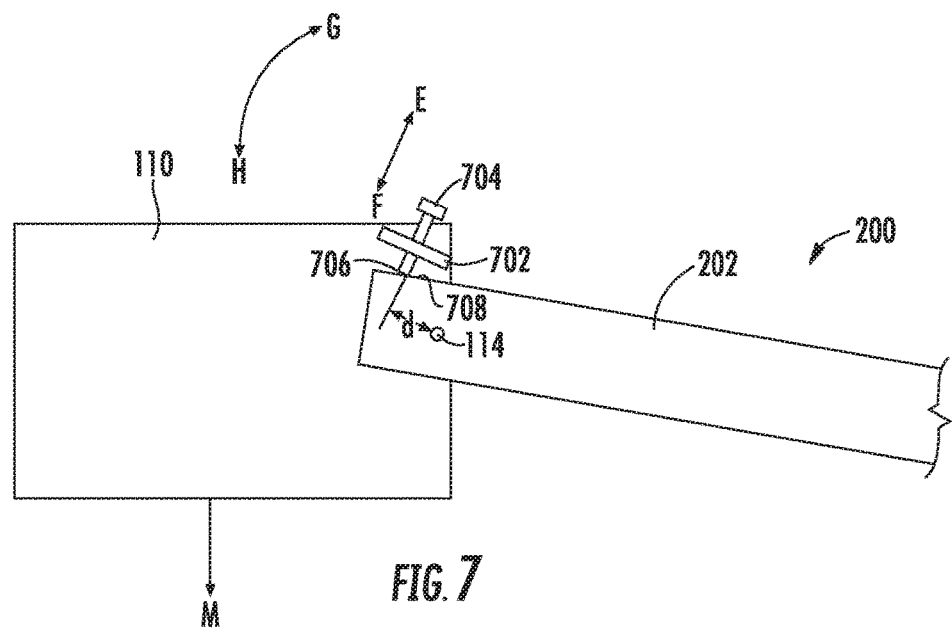
FIG. 7 is a side view of a virtual reality headset connected to a first band portion by a pivot, wherein the virtual reality headset includes an adjustable stop.

As discussed above, in various embodiments, the retention apparatus 200 can be attached to the head-mounted device 110 via pivots. FIG. 7 illustrates a side view of a head-mounted apparatus 110 and the left band portion 202 of the retention apparatus 200 wherein the head-mounted device 110 is connected to the left band portion 202 via a pivot 114. The pivot 114 could be, e.g., a rivet extending through the left band portion 202 and a flanged or other surface of the head-mounted device 110. The right band portion 206, not shown in FIG. 7, also includes a pivot 114 in this embodiment. The pivots 114 enable rotation of the head-mounted device 110 relative to the retention apparatus 200 about the pivot 114 in the direction of arrows G and H. Such rotation could allow a user to adjust the position of the retention apparatus 200 on the head 100.

The head-mounted device 110 and/or the retention apparatus 200 can include an adjustable stop to limit rotation of the head-mounted device 110 about the pivot 114 relative to the retention apparatus 200. FIG. 7 illustrates an adjustable stop 704, which is arranged as a threaded fastener (e.g., a bolt) passing through a threaded hole in a flange 702 attached to the head-mounted device 110. An end 706 of the adjustable stop 704 abuts an edge 708 of the left band portion 202 of the retention apparatus 200 at a distance d from the pivot 114. As the head-mounted device 110 rotates in the direction of arrow H about the pivot 114, the end 706 of the adjustable stop 704 contacts the edge 708 of the left band portion 202. The contact between the end 706 of the adjustable stop 704 and the edge 708 of the left band portion 202 stops further rotation of the head-mounted device 110 relative to the left band portion 202. By adjusting the adjustable stop 704 (e.g., turning the threaded fastener clockwise or counterclockwise), the degree to which the head-mounted device 110 can rotate in the direction of arrow H can be adjusted. The right side of the head-mounted device 110 and the right band portion 206 (not shown in FIG. 7) can have a similar adjustable stop 704. Referring to FIG. 7 and again to FIG. 1, the head-mounted device 110 has a mass M that is generally in front of the user's head 110 and in front of the pivots 114 such that the head-mounted device 110 will rotate in the direction of arrow H until it contacts the user's face. Such contact could result in uncomfortable pressure being applied to the user's face. The adjustable stops 704 can be adjusted to prevent the head-mounted device 110 from rotating in the direction of arrow H to a degree that the head-mounted device 110 applies an uncomfortable amount of pressure to the user's face.

Figure 8:
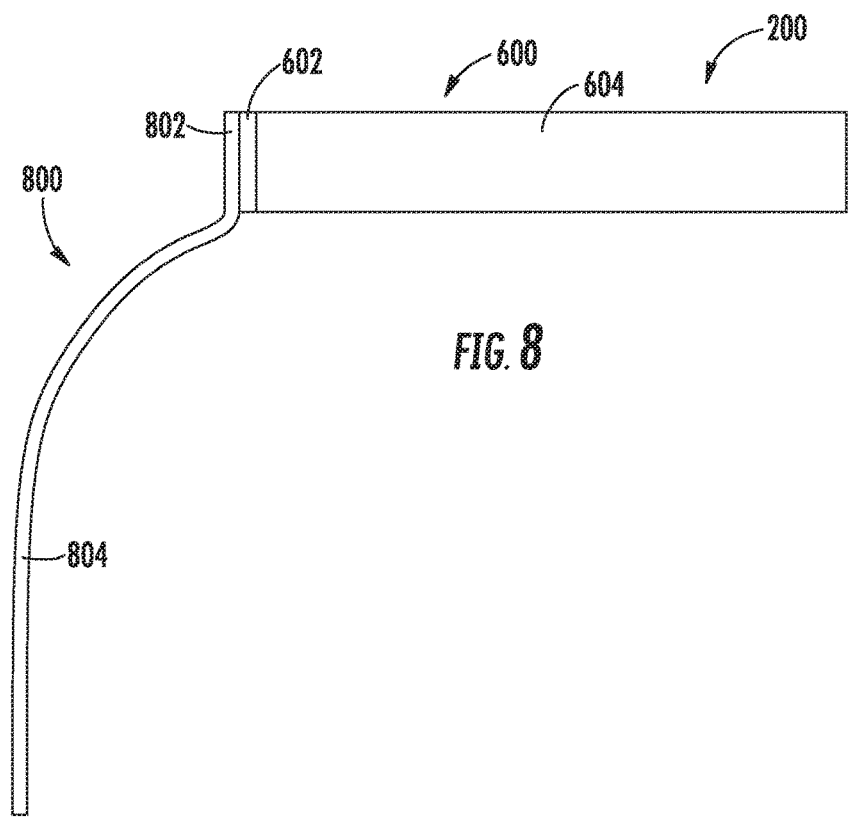
FIG. 8 is a side view of a band, according to one embodiment, with a face shield attached thereto.

In the above described embodiments, the head-mounted device 110 supported by the retention apparatus 200 has been described as a virtual-reality display. In various embodiments, the head-mounted device 110 could be an object or device other than a virtual-reality display. For example, FIG. 8 illustrates an embodiment in which the retention apparatus 200 supports a face shield 800. In the illustrated embodiment in FIG. 8, the retention apparatus 200 uses the band 600 illustrated in FIG. 6. The face shield 800 includes a flange 802 that is attached to the forehead portion 602 of the band 600 and a transparent shield 804 that extends from the flange 802. Such a transparent shield 804 may be used by surgeons or lab professionals, for example. In other applications, the retention apparatus 200 could be used with other head-mounted devices, such as welder's masks, hardhats, night vision goggles, bicycle helmets, or batting helmets.

In the embodiments discussed herein, a head-mounted device is secured to a user's head 100 via a retention apparatus 200 that includes elastic straps that allow for adjustable elastic tension. By increasing the amount of stretch in the elastic straps, semi-rigid, resilient band portions extending around at least portions of the user's head 102 are pulled tightly against the user's head, and the head-mounted device 110 at the user's forehead 104 and a band housing 250 at the back 102 of the user's head are more tightly clamped to the user's head 100. The elasticity of the tension allows the retention apparatus 200 to adjust to temporary deformations of the user's head 102 caused by, for example, frowning, laughing, coughing, yawning, or talking, such that the retention apparatus 200 remains comfortable.

While the foregoing is directed to embodiments of the present invention, other and further embodiments of the invention may be devised without departing from the basic scope thereof, and the scope thereof is determined by the claims that follow.

What is claimed is:

1. A retention apparatus for supporting a head-mounted device, the retention apparatus comprising:
a left band portion configured for arrangement along a left side of a wearer's head, wherein the left band portion comprises a resilient material, and wherein the left band portion includes a first device end configured for attachment to the head-mounted device and a first free end portion configured for arrangement toward a back side of the wearer's head;
a right band portion configured for arrangement along a right side of the wearer's head, wherein the right band portion comprises the resilient material, and wherein the right band portion includes a second device end configured for attachment to the head-mounted device and a second free end portion configured for arrangement toward the back side of the wearer's head;
an adjustment mechanism configured for arrangement at the back side of the wearer's head, wherein the adjustment mechanism includes an adjustment housing, a first arm, and a second arm, and wherein the first arm and second arm are selectively adjustable into and out of the adjustment housing in a telescoping manner;
a left elastic strap that includes a first end and an opposing second end, wherein the first end is directly connected to the left band portion, and wherein the second end is directly connected to the first arm of the adjustment mechanism; and
a right elastic strap that includes a third end and an opposing fourth end, wherein the third end is directly connected to the right band portion, and wherein the fourth end is directly connected to the second arm of the adjustment mechanism,
wherein selective adjustment of the first and second arms into the adjustment housing is configured to increase tension on the left and right elastic straps and thereby pull the first and second free end portions of the respective left and right band portions toward each other, and wherein selective adjustment of the first and second arms out of the adjustment housing is configured to decrease tension on the left and right elastic straps and thereby enable the first and second free end portions of the respective left and right band portions to move apart.

2. The retention apparatus of claim 1, wherein the first free end portion and the second free end portion overlap.

3. The retention apparatus of claim 2, further comprising a band housing attached to the adjustment mechanism, wherein the band housing includes a channel therethrough, and wherein the first free end portion and the second free end portion are arranged in the channel.

4. The retention apparatus of claim 3, wherein the band housing includes a padding material covering at least a portion of the band housing.

5. The retention apparatus of claim 3, wherein the left band portion and the right band portion include respective slots arranged toward the first and second free end portions, respectively, and wherein the band housing includes a pin extending through the slots in the first and second free end portions.

6. The retention apparatus of claim 1, wherein the first device end of the left band portion is opposite the first free end portion, wherein the first device end is configured to be attached to a left side of the head-mounted device, wherein the second device end of the right band portion is opposite the second free end portion, and wherein the second device end is configured to be attached to a right side of the head-mounted device.

7. The retention apparatus of claim 1, wherein the left band portion and the right band portion are connected to a forehead band portion configured for arrangement on the wearer's forehead.

8. The retention apparatus of claim 7, wherein the left band portion, the right band portion, and the forehead band portion are unitary.

9. A head-mounted apparatus, comprising:
a face-mounted device configured for arrangement over at least a portion of a wearer's face;
a left band portion configured for arrangement along a left side of the wearer's head, wherein the left band portion comprises a resilient material, and wherein the left band portion includes a first device end attached to a left side of the face-mounted device and a first free end portion that is positioned opposite the first device end and is configured for arrangement toward a back side of the wearer's head;
a right band portion configured for arrangement along a right side of the wearer's head, wherein the right band portion comprises the resilient material, and wherein the right band portion includes a second device end attached to a right side of the face-mounted device and a second free end portion that is positioned opposite the second device end and is configured for arrangement toward the back side of the wearer's head;
an adjustment mechanism configured for arrangement at the back side of the wearer's head, wherein the adjustment mechanism includes an adjustment housing, a first arm, and a second arm, and wherein the first arm and second arm are selectively adjustable into and out of the adjustment housing in a telescoping manner;
a left elastic strap that includes a first end and an opposing second end, wherein the first end is directly connected to the left band portion, and wherein the second end is directly connected to the first arm of the adjustment mechanism; and
a right elastic strap that includes a third end and an opposing fourth end, wherein the third end is directly connected to the right band portion, and wherein the fourth end is directly connected to the second arm of the adjustment mechanism,
wherein selective adjustment of the first and second arms into the adjustment housing is configured to increase tension on the left and right elastic straps and thereby pull the first and second free end portions of the respective left and right band portions toward each other, and wherein selective adjustment of the first and second arms out of the adjustment housing is configured to decrease tension on the left and right elastic straps and thereby enable the first and second free end portions of the respective left and right band portions to move apart.

10. The head-mounted apparatus of claim 9, wherein the first free end portion and the second free end portion overlap.

11. The head-mounted apparatus of claim 10, further comprising a band housing attached to the adjustment mechanism, wherein the band housing includes a channel therethrough, and wherein the first free end portion and the second free end portion are arranged in the channel.

12. The head-mounted apparatus of claim 11, wherein the band housing includes a padding material covering at least a portion of the band housing.

13. The head-mounted apparatus of claim 11, wherein the left band portion and the right band portion include respective slots arranged toward the first and second free end portions respectively, and wherein the band housing includes a pin extending through the slots.

14. The head-mounted apparatus of claim 9, wherein the first device end of the left band portion is opposite the first free end portion, wherein the first device end is attached to the left side of the head-mounted device, wherein the second device end of the right band portion is opposite the second free end portion, and wherein the second device end is attached to the right side of the head-mounted device.

15. The head-mounted apparatus of claim 9, wherein the face-mounted device is a virtual reality display.

16. The head-mounted apparatus of claim 9, wherein the face-mounted device is a face shield.

17. The head-mounted apparatus of claim 9, wherein the first device end is attached to the left side of the face-mounted device by a first pivot and the second device end is attached to the right side of the face-mounted device by a second pivot, and wherein the face-mounted device can be pivotably positioned relative to the left band portion and the right band portion about the first and second pivots.

18. The head-mounted apparatus of claim 17, further comprising an adjustable stop configured to limit a range of positions of the face-mounted device relative to the left band portion and the right band portion about the first and second pivots.

19. A head-mounted apparatus, comprising:
a head band that includes a left band portion configured for arrangement along a left side of a wearer's head, a right band portion configured for arrangement along a right side of the wearer's head, and a forehead portion configured for arrangement along the wearer's forehead, wherein the head band comprises a resilient material, wherein the left band portion includes a first free end portion configured for arrangement toward a back side of the wearer's head, and wherein the right band portion includes a second free end portion configured for arrangement toward the back side of the wearer's head;
a face-mounted device connected to the forehead portion of the head band and configured for arrangement over at least a portion of the wearer's face;
an adjustment mechanism configured for arrangement at the back side of the wearer's head, wherein the adjustment mechanism includes an adjustment housing, a first arm, and a second arm, and wherein the first arm and second arm are selectively adjustable into and out of the adjustment housing in a telescoping manner;
a left elastic strap that includes a first end and an opposing second end, wherein the first end is directly connected to the left band portion, and wherein the second end is directly connected to the first arm of the adjustment mechanism; and
a right elastic strap that includes a third end and an opposing fourth end, wherein the third end is directly connected to the right band portion, and wherein the fourth end is directly connected to the second arm of the adjustment mechanism,
wherein selective adjustment of the first and second arms into the adjustment housing is configured to increase tension on the left and right elastic straps and thereby pull the first and second free end portions of the respective left and right band portions toward each other, and wherein selective adjustment of the first and second arms out of the adjustment housing is configured to decrease tension on the left and right elastic straps and thereby enable the first and second free end portions of the respective left and right band portions to move apart.

20. The head-mounted apparatus of claim 19, wherein the first free end portion and the second free end portion overlap.

* * * * *

UNITED STATES PATENT AND TRADEMARK OFFICE
CERTIFICATE OF CORRECTION

PATENT NO. : 10,357,401 B2  
APPLICATION NO. : 15/282983  
DATED : July 23, 2019  
INVENTOR(S) : Jonathan R. Hsu et al.

Page 1 of 1

It is certified that error appears in the above-identified patent and that said Letters Patent is hereby corrected as shown below:

On the Title Page

Item (57), in Column 2, in "Abstract", Line 11, delete "includes arms the telescope into" and insert -- includes the arms which telescope into --, therefor.

In the Specification

In Column 5, Line 5, delete "FIG. 1," and insert -- FIG. 1. --, therefor.

In the Claims

In Column 13, Line 4, in Claim 13, delete "portions" and insert -- portions, --, therefor.

Signed and Sealed this
Twenty-fourth Day of September, 2019

Andrei Iancu
*Director of the United States Patent and Trademark Office*